(12) United States Patent
Bliss et al.

(10) Patent No.: US 9,568,375 B2
(45) Date of Patent: Feb. 14, 2017

(54) METHOD AND APPARATUS FOR ESTIMATING FOULING FACTOR AND/OR INVERSE SOLUBLE SCALE THICKNESS IN HEAT TRANSFER EQUIPMENT

(71) Applicant: Solenis Technologies, L.P., Schaffhausen (CH)

(72) Inventors: Terry Lynn Bliss, Wilmington, DE (US); Timothy Frederick Patterson, Wilmington, DE (US)

(73) Assignee: Solenis Technologies, L.P. (CH)

( * ) Notice: Subject to any disclaimer, the term of this patent is extended or adjusted under 35 U.S.C. 154(b) by 483 days.

(21) Appl. No.: 14/105,323

(22) Filed: Dec. 13, 2013

(65) Prior Publication Data

US 2014/0177673 A1  Jun. 26, 2014

Related U.S. Application Data

(60) Provisional application No. 61/739,785, filed on Dec. 20, 2012.

(51) Int. Cl.
*G01K 7/00* (2006.01)
*G01K 1/16* (2006.01)
(Continued)

(52) U.S. Cl.
CPC .............. *G01K 1/16* (2013.01); *F28G 15/003* (2013.01); *G01N 17/008* (2013.01); *G01N 25/18* (2013.01)

(58) Field of Classification Search
USPC .............................. 374/137, 7, 148, 166, 112
See application file for complete search history.

(56) References Cited

U.S. PATENT DOCUMENTS

| | | | |
|---|---|---|---|
| 3,913,378 A | * | 10/1975 | Hausler .................... G01B 7/06 374/7 |
| 4,396,300 A | | 8/1983 | Characklis et al. |

(Continued)

*Primary Examiner* — Mirellys Jagan
(74) *Attorney, Agent, or Firm* — Joanne Rossi; Michael Herman

(57) ABSTRACT

Scale deposition on a heat transfer surface in a liquid system such as a heat exchanger is estimated by directing of small portion of the liquid flow through a test cell, consisting of a sensor positioned on and projecting through a conduit wall. The sensor consists of a conductive block containing a heater and having a heated wetted test surface that is flush with the inside of the conduit wall and in contact with the flow through the conduit. Within the conductive block are two temperature sensors which are at different distances from the heated wetted test surface and the heater. The periphery of the apparatus is designed to reduce heat flow through the periphery and allow greater heat flow through the heated wetted test surface. By comparing the temperature differential between the two temperature sensors to the differential when no scale is present, the presence of and amount of scale can be determined, based on reduced heat transfer through the heated wetted surface caused by the accumulated scale. The change in the temperature differential is directly proportional to the scale thickness for a given type of scale. When the thickness of the scale is determined by another means, the nature of the scale can be implied. The sensitivity of the measurement can be adjusted to accommodate a very wide range of bulk liquid or ambient temperature via adjustment of the heat flux through the provided secondary heat flux path.

27 Claims, 15 Drawing Sheets

(51) Int. Cl.
*F28G 15/00* (2006.01)
*G01N 25/18* (2006.01)
*G01N 17/00* (2006.01)

(56) References Cited

U.S. PATENT DOCUMENTS 6,386,272 B1 * 5/2002 Starner ................ G01B 21/085
  165/11.1
8,147,130 B2   4/2012 Sakami et al.

* cited by examiner

METHOD AND APPARATUS FOR ESTIMATING FOULING FACTOR AND/OR INVERSE SOLUBLE SCALE THICKNESS IN HEAT TRANSFER EQUIPMENT

CROSS-REFERENCE TO RELATED APPLICATIONS

This application claims the benefit of and priority to U.S. Provisional Application Ser. No. 61/739,785, filed Dec. 20, 2013 and entitled "METHOD AND APPARATUS FOR ESTIMATING FOULING FACTOR AND/OR INVERSE SOLUBLE SCALE THICKNESS IN HEAT TRANSFER EQUIPMENT", the disclosure of which is incorporated by reference herein in its entirety.

BACKGROUND OF THE INVENTION

Industrial plants, such as power plants, steel mills, pulp or paper making plants, have relatively complex water/fluid systems. Organic and inorganic matter deposits on the inner walls of these systems forming an accumulation of fouling or scaling deposits which interfere with the proper operation of the system. This is particularly severe on heated surfaces such as heat exchanger surfaces. This is an unwanted occurrence that causes a number of operational problems such as inadequate heat exchange, plugging of equipment, inefficient usage of chemicals, increased utility costs, lost production due to downtime, corrosion, and downgraded products from increased dirt counts.

In principle, one can distinguish between fouling deposits on the one hand and scaling deposits on the other hand. Fouling deposits are organic deposits which often occur in the form of biofilms in aqueous systems. Such biofilms substantially consist of micro-organisms, e.g. bacteria, algae, fungi and protozoa. Scale is formed from inorganic matter such as complexes of calcium (carbonate, oxalate, sulfate, silicates), aluminum (silicates, hydroxides, phosphates), barium sulfate, radioactive radium sulfate, and silicates of magnesium.

In order to avoid the accumulation of fouling deposits and in particular the growth of biofilms, biocides are added into the fluid concerned as countermeasures. Scale deposits can be removed or prevented by adding chemical deposit control agents based on homopolymers, copolymers and terpolymers of acrylic acid, methacrylic acid, maleic acid and aspartic acid. Chemical deposit control agents include organic phosphonates and their derivatives, as well as polyphosphates. The dosage of these biocides and chemical deposit control agents should be controlled very carefully because they are very expensive.

In line sensors are particularly useful in detecting and quantifying scale for controlling the addition of scale treatment additives. High temperature scaling conditions present a significant challenge to developing an in line scale sensor. Such flows generally preclude the use of most non-metal materials for any surface that is in contact with the flow, and also can be challenging environments for proper operation of electronic components. In addition, the liquid comprising the flow may have other properties that make sensor development difficult; the flow can contain particulates, be toxic, be corrosive to some material, not have constant density, etc. For example, cooling water may have a significant content of dissolved salts, but it is still called water. In many industries, water with a high content of dissolved salts may be called brine, although that term is usually applied to solutions of highly soluble salts. In pulp producing mills, water with certain dissolved salts and dissolved lignin may be called black liquor. Even solutions of highly soluble salts can accumulate troublesome amounts of inverse soluble salts that accumulate in the water for various reasons. Since the most common scale type is inverse soluble scale, the sensor needs to have a surface exposed to the flow that is at a higher temperature than the bulk liquid flow. This requires some form of heating, to produce a heated wetted test surface that is predisposed for the accumulation of scale. The heating must be accomplished in a manner that allows the accumulation to be quantified. This quantification may be a measurement of the reduced heat transfer capabilities resulting from the accumulation, or of the thickness of the accumulation, or both.

SUMMARY OF THE INVENTION

The present invention is premised on the realization that fouling factor (reduced heat transfer effectiveness due to the buildup of inverse soluble scale on a heat transfer surfaces) can be estimated by diverting a small amount of working fluid through a flow cell, across a heated wetted test surface, in which the heated wetted test surface temperature and the flow conditions over it mimic the heat transfer surface of interest. The heated wetted test surface is either an integral part of a block of material capable of conducting heat (conductive block) or is in intimate contact with said block. Heat is supplied to the conductive block by a simple cartridge heater contained at least partially within the conductive block, or by other appropriate means. The conductive block is provided with insulation around it such that the primary heat conduction plate is toward the heated wetted test surface and such that there is at least one secondary heat conduction path away from the heated wetted test surface. As scale accumulates on the heated wetted test surface, the scale presents an added resistance to heat transfer towards the heated wetted test surface. The heat transfer resistance along the secondary heat conduction path is not affected by the accumulation of scale. Therefore, as scale accumulates there is reduced heat transfer toward the heat wetted test surface and increased heat transfer along the secondary heat conduction path. Measurement of the heat transfer resistance added by the scale on the heated wetted test surface is taken as an indication of the severity of scale on the heat transfer surface.

The surface temperature of the flow cell heated wetted test surface is estimated by the use of two highly accurate temperature sensors/transmitters, which are spaced at a known distance from each other and at different and known distances from the heated wetted test surface and the heat source, within a conductive block. A heat conduction coefficient (k) for the conductive material comprising the block is calculated from the temperature difference reported by the two temperature transmitters ($T_1$ and $T_2$) and the known distance between them. The surface temperature of the heated wetted test surface is then estimated from the conduction coefficient and the distance from either temperature transmitter to the heated wetted test surface. As inverse soluble scale accumulates on the heated wetted test surface, the scale provides an additional restriction to the heat flow path through the conductive block to the heated wetted test surface, thus raising the temperature within the block as measured by both temperature transmitters. With a higher internal temperature, more heat exits via the secondary heat conduction path. This results in a reduced temperature differential between the two temperature transmitters, because less heat energy is exiting through the heated wetted test surface. If the temperature at the end of the secondary heat conduction path is constant or nearly so, the temperature difference between the two temperature transmitters in the conductive block is linear with the fouling factor which results from the accumulated scale on the heated wetted test surface, and indicative of the likely degree of fouling or scaling on the commercial heat transfer surface it emulates. The temperature differential between the two temperature transmitters is also linear with the scale thickness for any particular type of scale, but the relationship constant between temperature differential between the two temperature transmitters and scale thickness is different for different types of scale (e.g. calcium carbonate vs. calcium sulfate or calcium phosphate).

In a further embodiment, scale thickness on the heated wetted test surface can be concurrently measured via a pulsed ultrasonic signal, on the principle of time of flight reduction due to reduced distance for the ultrasonic pulse to travel to the scale and then return to the ultrasonic probe, as scale accumulates.

The range of the temperature differential between the two temperature transmitters can be controlled by many means, including varying the distance between the temperature transmitters, the temperature of the heater, the thickness of the insulation along the secondary heat conduction path, the heat conduction properties of the material from which the secondary heat path is constructed, the existence of more than one secondary heat conduction path, the temperature at the end of or along the secondary heat conduction path, addition of a layer of material with a different heat transfer coefficient as the heated wetted metal surface, or even the addition of heat or cooling at the end of the secondary heat conduction path.

By adjusting these variables, a usefully accurate indication of fouling factor can be determined across a very wide range of bulk liquid temperatures, bulk liquid flow rates, heater temperatures, and ambient environment surrounding the apparatus. When combined with an optional ultrasonic or other scale thickness indication, useful insight into the nature of the deposit can be inferred. This allows the scale control treatment to be adjusted in a more appropriate manner, to optimize heat transfer and minimize cost for a specific commercial heat transfer installation.

The objects and advantages of the present invention will be further appreciated in light of the following detailed description and drawings in which:

DETAILED DESCRIPTION

Figure 1:
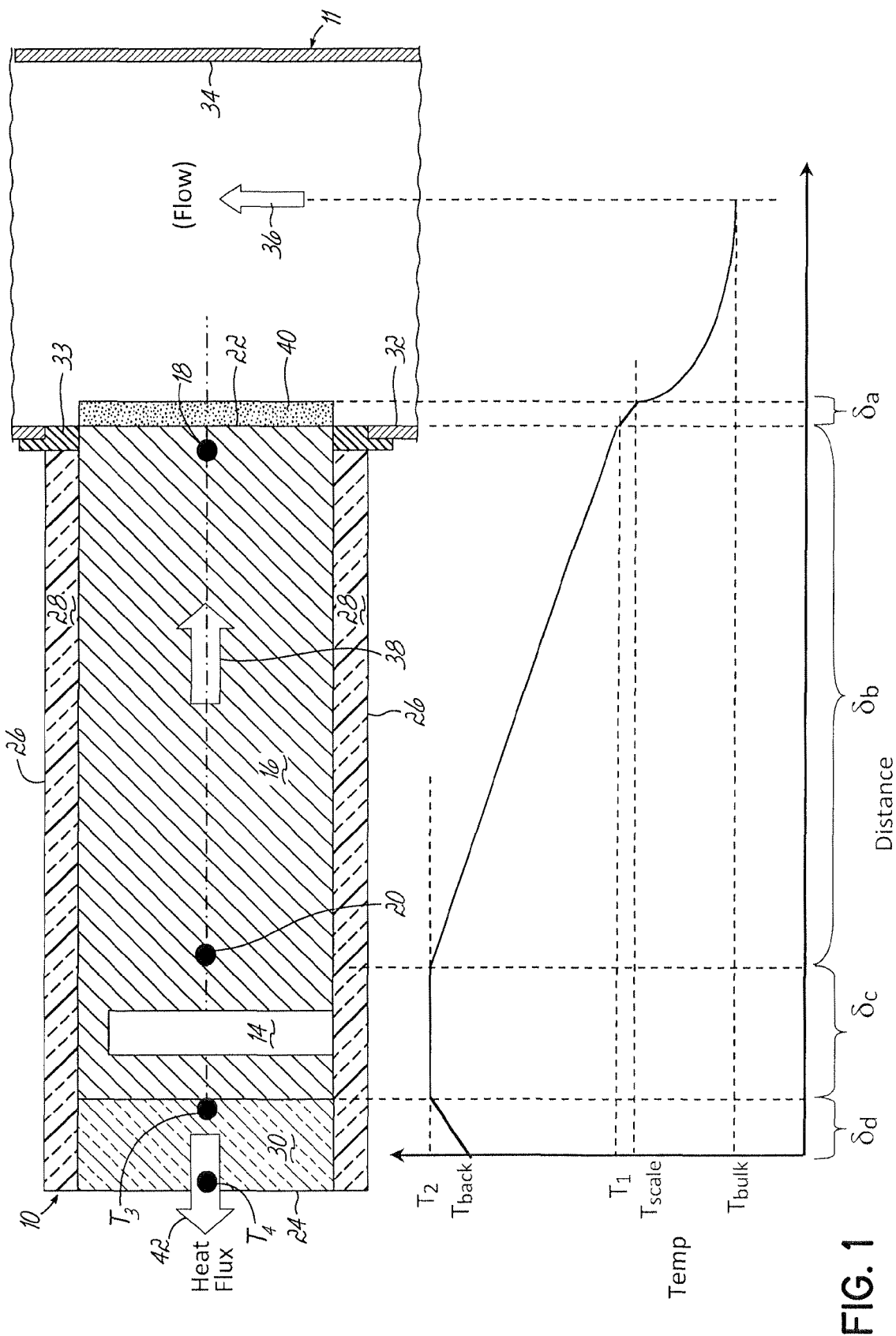
FIG. 1 is a diagrammatic depiction of the present invention with an indication of temperature sensor locations.

As shown in FIG. 1, an apparatus or sensor 10 used to detect scale formation on surfaces of a water system is located in a side conduit 11 of a water system. This side channel 11 takes water from the water system and subsequently returns this to the water system. The water system (not shown) can be any industrial water treatment system, such as a power plant, oil refinery, paper mill, or steel mill. The sensor is designed to measure scale accumulation on a surface with a temperature higher than the temperature of the bulk water.

The sensor 10 includes a heater 14 positioned within a conductive block 16 which includes a first temperature sensor 18 located at a first position in the metal block and a second temperature sensor 20 positioned within the conductive block 16. The first temperature sensor 18 is positioned near a heated wetted test surface at a first end 22 of the block, and the second temperature sensor 20, as shown, is near the heater 14. The apparatus further includes a second end 24 opposite the heated wetted test surface at the first end 22, which is as shown is exposed to ambient conditions. Heater 14 is a cartridge heater, which is positioned within conductive block 16 and which allows heat flow toward and away from the heated wetted test surface 22. Although it can be formed from any suitable material, it will generally be metal. As shown, the heated wetted test surface 22 is in contact with the bulk water flow and therefore serves as the test surface, specifically the heated wetted test surface.

The apparatus 10 has four peripheral sides 26 (two shown). The peripheral sides 26 include an insulation layer 28 and the second end 24 includes an insulation layer 30 which may have a different heat conductivity than the insulation layer 28.

The apparatus 10 is fixed to conduit 11 having walls 32 and 34, with the heated wetted test surface at the first end 22 of conductive block 16 attached to the wall 32, by means of appropriate fasteners such as screws, bolts, or clamps (not shown), but insulated from direct contact with wall 32 by means of insulation 33 to avoid conductive heat transfer. Ideally no heat is transferred from block 16 to wall 32 of conduit 11. If little or no heat is transferred from the conductive block 16 to wall 32 of conduit 11, the temperature across the heated wetted test surface 22 will be relatively even, and so will produce a more representative indication of the much larger commercial heat transfer surface it is attempting to emulate. The heated wetted test surface is flush with the inside surface of the side 32 of conduit 11 to minimize the disruption of flowing bulk liquid 36 in conduit 11.

As shown, the conduit 11 is rectangular in shape. The conduit 11 directs fluid from a water system (not shown), particularly one which has a heated surface, such as a heat exchanger. The conduit simply draws off bulk water which flows in the direction of arrow 36 through the conduit 11, ideally at flow conditions comparable to those in the commercial heat transfer equipment it is intended to emulate.

In operation, the heater 14 generates heat flow or heat flux as shown by arrow 38 towards the heated wetted test surface 22. Test surface 22 is heated to a temperature approximating the temperature of the section of the heat exchanger or other water system heat transfer surface it is to emulate. Thus, the heated wetted test surface 22 is heated by the heater and wetted by the flow of fluid through conduit 11. As a result, there is a likelihood that a layer of scale 40 will form on the heated wetted surface 22. Temperature sensor 18 will record the temperature $T_1$ near the heated wetted surface 22. The second temperature sensor 20 will report the temperature $T_2$ of block 16 adjacent the heater 14. Since the heater 14 is located within the conductive block 16, heat can flow outwardly from the second end 24 of the apparatus 10 as shown by arrow 42. This is the secondary heat conduction path.

When the heater 14 is activated, initially heat flow will be in the direction of arrow 38 and $T_2$ will be recorded, and subsequently $T_1$, which should be less than $T_2$. As heat passes through the wetted surface 22 into the bulk flow as represented by arrow 36, in other words, the heated wetted test surface is being cooled down, in turn making $T_1$ less than $T_2$.

As scale 40 builds up on heated wetted test surface 22, less heat will flow through the end 22 of the block 16. The scale 40 acts as an insulator; heat transfer resistance is increased. Because the heat can travel rearwardly in the direction of arrow 42, the temperature $T_1$ and $T_2$ will both increase because of reduced heat flow through the heated wetted test surface 22 due to the insulation effect of the scale 40. However, since the temperature of block 16 is now higher, more heat energy will escape through the partially insulated second end 24 of block 16, the secondary heat conduction path. This will reduce the temperature differential between $T_1$ and $T_2$ and provide an indication of scale formation, and the magnitude of the change in the temperature differential is an indication of the amount of scale, and, in particular, the negative impact of the scale on the heat transfer through the heated wetted test surface 22 of block 16.

The heat transfer is governed by the following equations $$\frac{q_{scale}}{A} = K\left(\frac{T_2 - T_1}{\delta_b}\right),$$

$$\frac{q_{total}}{A} = K\left(\frac{T_3 - T_4}{\delta_d}\right),$$

$$\frac{q_{total}}{A} = \frac{q_{scale}}{A} + \frac{q_{insul}}{A}$$

K is the conduction heat transfer coefficient for the respective materials, scale, insulation and metal. A is area, and q is the heat flux of heat energy. The heat transfer is two directional, in the direction of arrow 38 (toward the heated wetted surface) and in the direction of arrow 42 (the opposite direction, through end 24, the partially insulated path to the ambient environment). As scale builds up on the heated wetted test surface 22, the "resistance" to heat transfer in the direction of the heated wetted test surface increases. The "resistance" to heat transfer in the opposite direction is unchanged, thus $q_{scale}$ decreases and $q_{insul}$ increases with the associated $\Delta Ts$ (both $T_2-T_1$ and $T_3-T_4$) changing accordingly and linearly with scale thickness. Either $T_2-T_1$ or $T_3-T_4$ could be used to estimate the accumulation of scale and its resulting heat transfer reduction.

Note that $T_4$ the temperature of the second end 24 will change with environmental conditions which will change the heat flux. Also the insulation along the peripheral surfaces 26 is assumed "perfect" which is not attainable in actual installations. There will be some radial heat flux in actual implementations and this heat flux will also be impacted by environmental conditions. In a non-quantitative sense, if the insulation of the peripheral surfaces 26 are assumed to be partially insulated also, as they would be in an actual installation, the combined area of end 24 and sides 26 can be conceptually thought of as the secondary heat conduction path.

Figure 2:
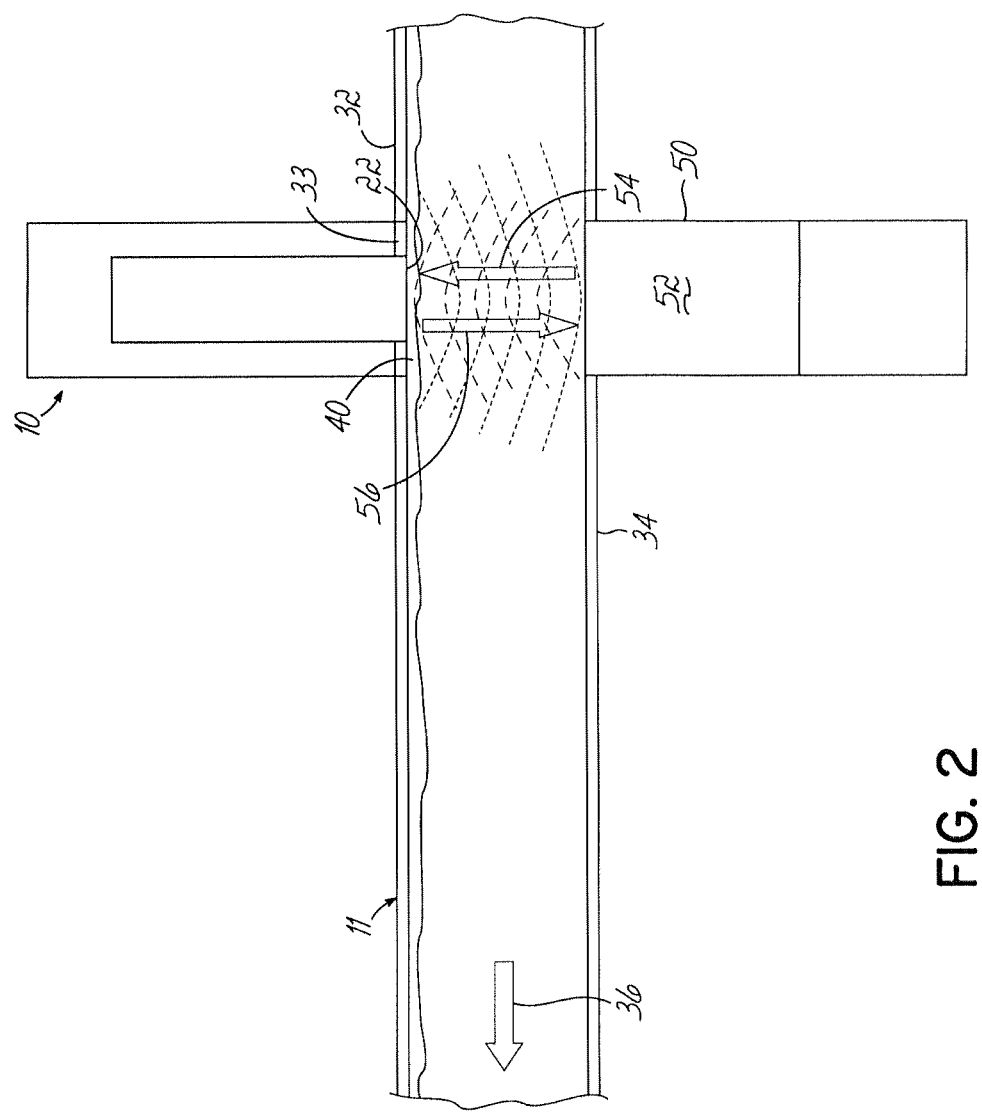
FIG. 2 is a diagrammatic view, partially in cross section, of an alternate embodiment of the present invention.

FIG. 2 shows an alternate embodiment of the present invention. The scale sensor 10 is incorporated on conduit 11, as shown in FIG. 1. In addition, a scale thickness measuring unit 50 is incorporated in wall 34 of conduit 11 directed at wall 32. The scale thickness measuring unit 50 is mounted in an opening in wall 34 of conduit 11 such that the surface of measuring unit 50 is flush with the inside surface of wall 34 of conduit 11 to minimize disruption of the flow 36. Any known means of attachment, such as screws or bolts, clamps, or threads (not shown) may be used. Since the thickness measuring unit 50 does not use a heater and is not involved in heat transfer, it is not necessary to insulate it from contact with the wall 34 of conduit 11.

The measuring unit 50 comprises an ultrasonic transducer 52 and a detector. The ultrasonic transducer is but one of several methods to detect the thickness of the deposit on surface 32. Any known apparatus can be employed in the present invention. With unit 50, an ultrasonic signal 54 is emitted by the transducer 52 towards wall 32. In order to detect and analyze fouling and/or scaling deposits 40 accumulated on the heated wetted test surface 22 of block 16, an ultrasonic reflection signal 56 which occurs through a reflection of the ultrasonic emission signal 54 is measured. If no deposits 40 are accumulated, heated wetted test surface 22 mainly serves as a reflecting surface for the ultrasonic signal. The measuring unit will measure the time required for the signal to travel to heated wetted test surface 22 and back. If scaling and/or fouling deposits 40 cover the reflecting heated wetted test surface 22, the ultrasonic signal is reflected at least partially at the surface of the deposits 40.

If scale is present, the reflected signal requires less time to return, due to the shorter distance it travels after reflecting off the scale surface than earlier, when no scale was present. The thickness of the scale can be calculated based on the difference between the current "time of flight" measurement and a previous reference measurement when no scale was present, and the speed at which sound travels through water.

There are many different types of compounds that can form scale, such as carbonates, oxylates, sulfates, silicates, of calcium, aluminum compounds such as silicates, hydroxides, phosphates, as well as others. The different types of scale have different densities and different heat transfer resistance coefficients per unit of scale thickness. By measuring the $q_{scale}$ and the thickness of the deposited scale, one can estimate the type of scale that is forming based on this empirical data. This will in turn allow the operator to apply appropriate remedial chemicals to the water system to remove or control that particular type of scale, or, in the event of a biofilm, the appropriate chemicals to treat the biofilm.

If only a biofilm is present, the reflected wave 56 will actually comprise a first small peak from reflection of the surface of the biofilm and a second higher peak from the reflection of the inner wall 32. The amplitudes of the two signals are different because the acoustic impedance of the biofilm is lower than the acoustic impedance of the wall material 32. The time difference between the two signals will indicate the thickness of the biofilm.

Scaling Tests

Figure 10:
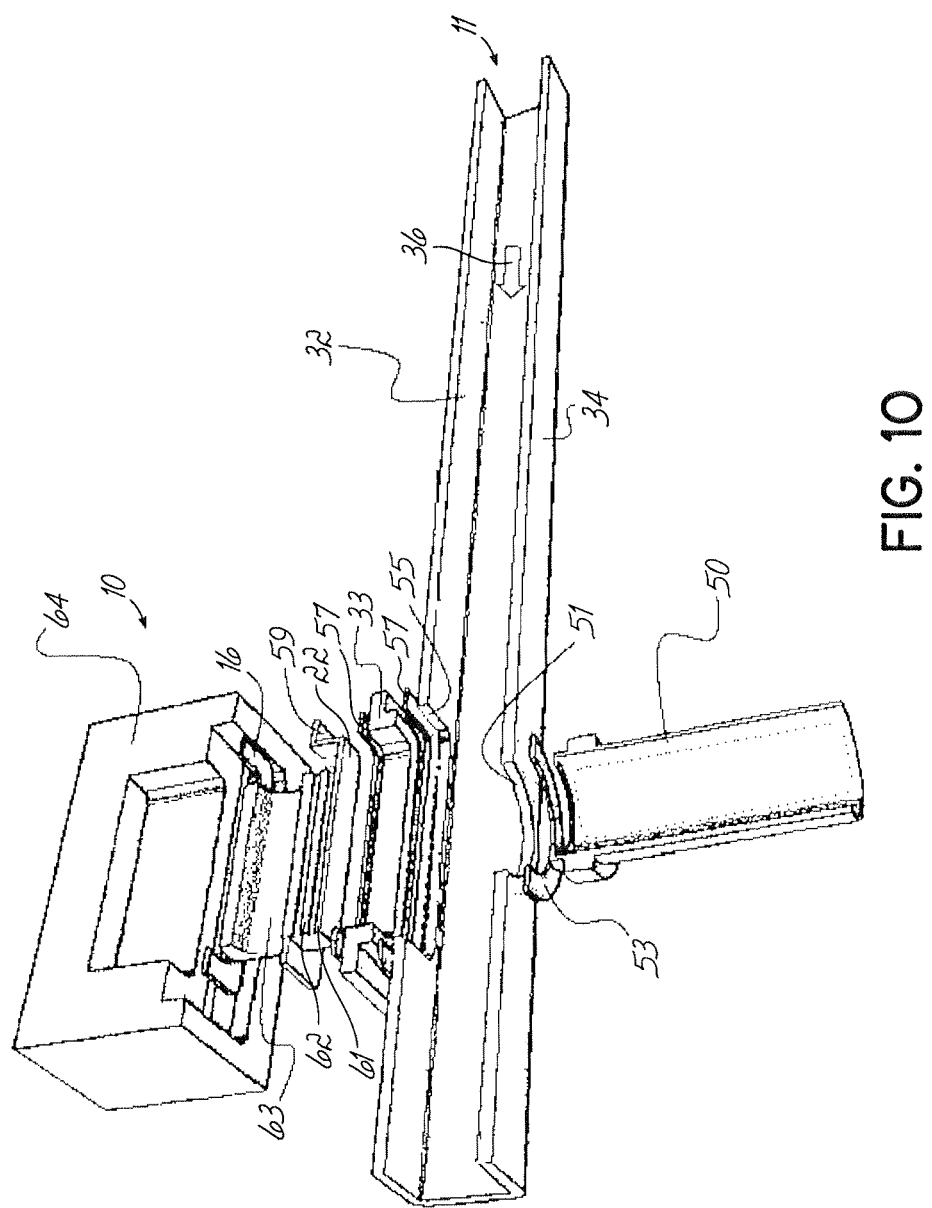
FIG. 10 is an exploded partial cutaway drawing of the particular embodiment of the device of the present invention used to produce the data found in the graph shown as FIG. 9.

The apparatus of FIG. 2 is shown in more detail in a cross sectional view shown at FIG. 10. In this embodiment, thickness measuring unit 50 is mounted in an opening 51 in wall 34 of conduit 11, separated from the wall by a gasket 53. Opposite the thickness measuring unit 50 is the sensor 10. As shown, it is mounted in an opening 55 of conduit wall 32, separated from the wall by a plastic insulater 33 which, in turn, is separated from the block 16 and the wall 32 by gaskets 57. The block 16 includes a mounting flange 59. Although the heat sensors are not shown, these would be located in channels 61 and 62 respectively, with the cartridge heater 14 located in enlarged channel 63. All of this is encased by a PEEK insulator 64.

The apparatus shown in FIG. 10 (which included a 200 watt cartridge heater, a CuNi heated wetted test surface, two RTD temperature transmitters, PEEK (Polyether ether ketone) insulation, and a pulsed ultrasonic transducer for measuring distance to the heated wetted test surface via "time of flight" difference) attached to a cooling tower was tested using water as the bulk liquid. Block 16 was constructed of CuNiFeMg alloy. The test surface was about 14 mm from the center line of the cartridge heater. RTD temperature transmitters $T_1$ and $T_2$ were about 3.5 mm centerline to centerline and were offset along the direction of the heat flux from the heater toward the test surface to avoid interference of one transmitter from the another. Salts were added to deionized water to simulate 4 times concentration of our standard makeup water (e.g., the water was formulated to simulate standard makeup water that had been "precycled" to 4 cycles of concentration) and the water was circulated through the tower system, and allowed to cycle up to a target 6 cycles of concentration. The composition of the "precycled" water, the tower makeup water, and the 6 cycles of concentration water are listed in Table 1.

TABLE 1

Cooling tower water data for the scaling trials, starting 20 Aug. 2012

| Water type | $Ca^{++}$ (as ppm $CaCO_3$) | $Mg^{++}$ (as ppm $CaCO_3$) | Total Alkalinity (as ppm $CaCO_3$) | $Cl^-$ (as ppm Cl) | $SO_4^-$ (as ppm $SO_4$) | Drew 2235 (ppm product) |
|---|---|---|---|---|---|---|
| Pre-cycled water (simulates 4 cycles of concentration) | 400 | 200 | 400 | 2856 | 192 | 110 |
| System makeup water | 100 | 50 | 100 | 714 | 48 | 27.5 |
| Target water (simulates 6 cycles of concentration) | 600 | 300 | 600 | 4284 | 288 | 165 |

The tower was maintained at 24.5 C bulk water temperature, and with conductivity-initiated blow down/and level-controlled makeup water addition to control conductivity at about 3500 μmho (6 cycles of concentration which was reached about 60 hours after the start of scale Trial 1). The flow velocity in the conduit 11 was 0.75 meters per second, pH was 9.0, and the heater power was set to produce a temperature of 60.5° C. on the heated wetted test surface. Trial 1 was conducted for a total of 96 hours (3.5 days). At the end of that time, the accumulated scale on the heated wetted test surface was cleaned off, and the test was restarted as Trial 2, with the same conditions, except the heater power was increased to produce a surface temperature of 70° C. on the heated wetted surface. The water in the cooling tower sump was already at 6 cycles of concentration at the start of Trial 2, and was maintained as such. Trial 2 was allowed to run for 168 hours (7 days), but after 121 hours (5 days) the amount of Drew 2235 antiscalant was increase by 50%.

Figure 9:
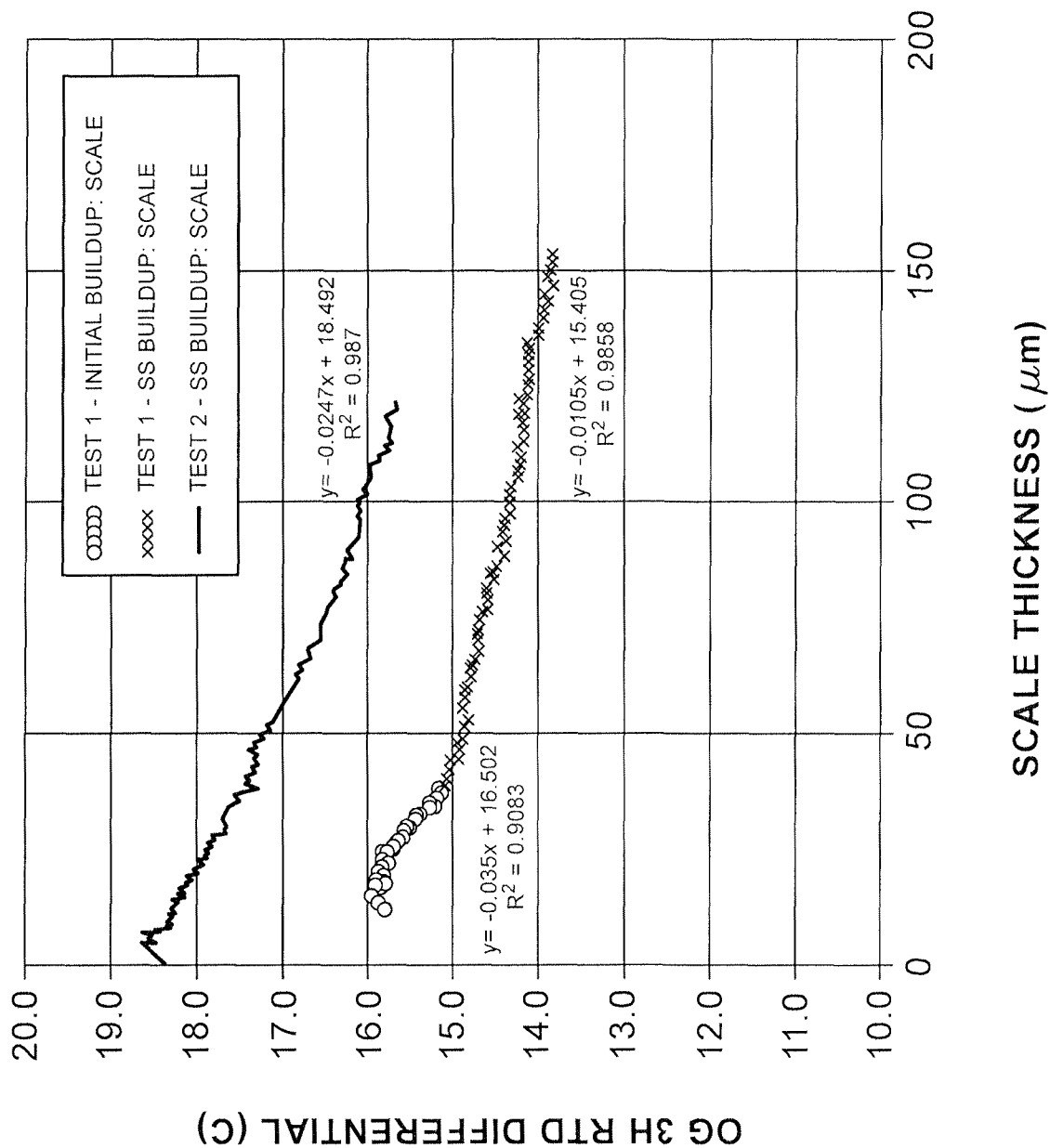
FIG. 9 is a graph showing a change in temperature differential as scale accumulates.

FIG. 9 shows the temperature differential between $T_2$ and $T_1$ plotted against scale build up thickness as measured with an ultrasonic transmitter and receiver. The response of the temperature differential is linear with scale thickness in the "prescale" buildup range of 0 to 45 μm, and also linear, but with a different slope, in the "steady state" range of 45-160 μm of scale thickness. During Trial 2, the response of temperature differential is linear with scale thickness across the entire range, but the absolute value of the temperature differential and the relationship coefficient (slope of the temperature differential vs. scale thickness plot) is different, because the insulating effect of the scale layer produces higher temperatures throughout the conducting block 16 and also higher temperature differentials between the two temperature measurements at higher heater power. A change in the addition rate of the antiscalant (Drew 2235) changes the rate of scale thickness accumulation vs. time (not shown) but not the relationship between temperature differential and scale thickness.

There were periods within both scaling trials where data was not available, due to data logging problems or other issues.

The temperature differential $(T_2-T_1)$ plotted against the scale thickness (as measured ultrasonically) is highly linear. In addition, the temperature difference $(T_2-T_1)$ is also highly linear when plotted against fouling factor, as determined with an Ashland OnGuard 2-Plus scale analyzer (plot not shown) which is widely used for monitoring fouling factor in commercial installations. In all cases, linearity is demonstrated by a linear correlation coefficient ($R^2$) of between about 0.91 and 0.99 (1.0 indicates perfect correlation and 0 indicates no correlation).

Thus, the embodiments shown in FIGS. 1, 2, and 10 adequately measure the scale formation along the heated wetted metal test surface. The concept can be further enhanced by modifying sensor 10 to compensate for variables, in particular ambient conditions surrounding sensor 10. FIGS. 3 through 8 show various modified temperature measuring units. All of these are attached to and protruding through wall 32 of conduit 11, with their heated wetted test surface 22 flush with the inside wall 32 of conduit 11 which directs fluid from the water system to the heated wetted test surface where scale is being measured. All must have an insulating element 33 to reduce the flow of heat from the conductive block to wall 32 of conduit 11. In these embodiments in FIGS. 3 to 8, like elements will retain like numerals from FIGS. 1 and 2. All of the depictions shown schematically in FIGS. 3-8 are intended to reduce the impact of variations of the ambient conditions surrounding the sensor 10, or increase the sensitivity of the scale quantification measurement through manipulation of heat transfer along the secondary heat conduction path(s), or both. They are most applicable when the device is installed outside of a climate-controlled room, or when the temperature of the flow 36 is much higher than that of the ambient temperature, or both. It is emphasized that in some cases the bulk flow might be other than industrial cooling water, e.g., black liquor in a pulp mill, brine, or other bulk flow fluids. In some cases, the temperature may be too high or the fluid may be otherwise unsuitable for measurement of the scale thickness via pulsed ultrasonic signal. In such cases, the invention may be used with a different scale thickness measuring means suitable for the environment, or without a means of measuring scale thickness. In cases where there is no suitable scale thickness measurement means available, only heat transfer resistance information will be obtained, and it will not be readily possible to infer the chemical composition of the scale.

Figure 3:
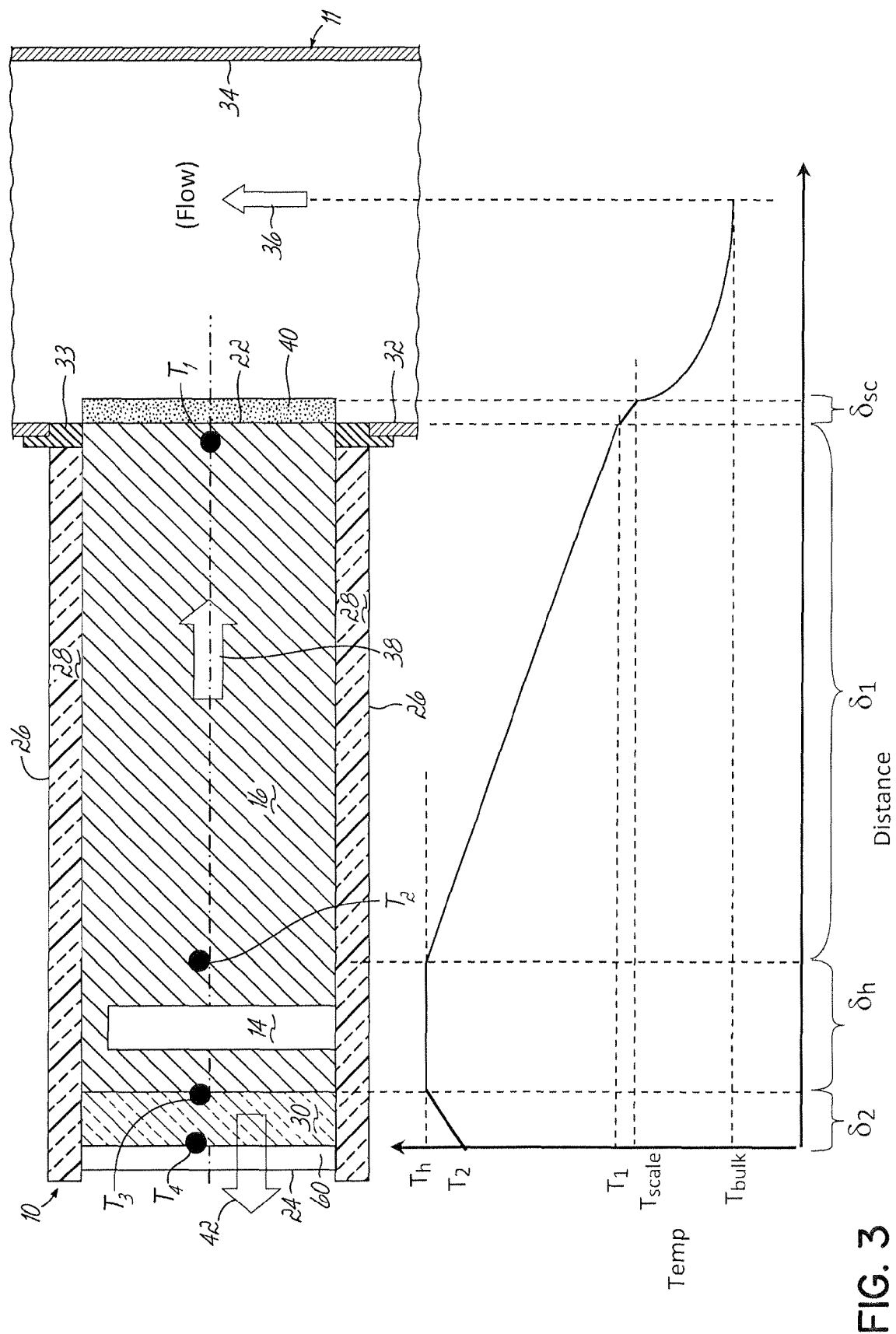
FIG. 3 is a diagrammatic view similar to FIG. 1 of a second alternate embodiment of the present invention.

The embodiment shown in FIG. 3 is a modified version of the embodiment shown in FIG. 1. The modification is the addition of a back heater 60 on the second end 24 opposite the wetted surface 32. The heat flux is governed by the similar equations $$\frac{q_{material1}}{A} = K\left(\frac{T_2 - T_1}{\delta_b}\right),$$

$$\frac{q_{material2}}{A} = K\left(\frac{T_3 - T_4}{\delta_d}\right),$$

$$\frac{q_{total}}{A} = \frac{q_{material1}}{A} + \frac{q_{material2}}{A}$$

Since $T_4$ is controlled there is the capability to actively control heat flux through insulation layer 30. The heat flux control along the secondary heat conduction path is accomplished by controlling temperature $T_4$.

Note the insulation 28 along the longitudinal surfaces is assumed "perfect" for this example, which is not attainable in actual installations. There will be some radial heat flux in actual implementations and this heat flux will be impacted by ambient conditions. The heat flux control depicted schematically in FIG. 3 can be called active heat flux control, because it is supplied with a controlled amount of external energy. As such, the power supplied by the back heater 60 may be adjusted or controlled based on the temperature $T_4$, which becomes a point of adjustment that can be used to optimize operation of the device when it must operate at more extreme conditions. A potential limitation of the device as depicted in FIG. 3 is the inability to cool surfaces 26 and 24 of sensor 10.

The following description is provided as an example of how to optimize the sensor design of FIG. 3 to maximize its utility for a given implementation. For purposes of this analysis, $T_2$ and $T_3$ are positioned immediately adjacent either side of heater 14. Since $T_2$ and $T_3$ are not in contact with the heater, it is assumed that $T_2=T_3=T_h$. ($T_h$ is temperature of the heater.) In addition, material 30 is extended from the surface of the heater 14 (the new location for sensor $T_3$) to the location of sensor $T_4$ (the interface between material 30 and heater 60); $\delta_2$ is now the distance between heater 14 and heater 60.

In any given implementation for this particular embodiment, the following will be known, bulk fluid temperature (which allows an estimate of temperature at the exposed surface of the scale. $T_{scale}$), and maximum available heater output. The optimization problem is to select material 16, material 30, distance $\delta_1$, $\delta_2$ and the temperature maintained by the backside heater 60 (which is equal to $T_4$) so that over the anticipated operating range of the sensor, the temperature differences $T_1$ and $T_3-T_4$ are maximized, thus providing the highest possible resolution for the scale accumulation measurement.

The heat flux balance for the sensor is given by $$\frac{q_T}{A} = \frac{q_{16}}{A} + \frac{q_{30}}{A}$$

where $g_T$ is the heater output, $q_{16}$ is the heat flux through material 16, $q_{30}$ is the heat flux through material 30 and A is the area. The equation can be restated using the resistance analogy $$\frac{q_{30}}{A} = \frac{T_h - T_4}{R_4}$$

$$\frac{q_{16}}{A} = \frac{T_h - T_{scale}}{R_{16-scale}}$$

to substitute for elements on the right hand side of the equation, yielding $$\frac{q_T}{A} = \frac{T_h - T_{scale}}{R_{16+scale}} + \frac{T_h - T_4}{R_{30}}$$

where $R_{16+scale}$ is the combined thermal resistance for material 16 and the scale and $R_{30}$ is the thermal resistance for material 30. The equation can be rearranged to provide an expression for $T_h$ $$\left[\frac{q_T}{A} + \frac{T_{scale}}{R_{16+scale}} + \frac{T_4}{R_{30}}\right]\left[\frac{1}{R_{1+scale}} + \frac{1}{R_{30}}\right]^{-1} = T_h$$

For a given material 16, material 30, and scale type the above equation can be used to calculate $T_h$. Once $T_h$ is calculated the two heat fluxes can be calculated as follows $$q_{16} = \frac{T_h - T_{scale}}{R_{16-scale}} A$$

where $$R_{16-scale} = \frac{\delta_1}{k_{16}} + \frac{\delta_{scale}}{k_{scale}}$$

and $$q_{30} = \frac{T_h - T_4}{R_4} A$$

where $$R_{30} = \frac{\delta_2}{k_{30}}$$

Once the heat fluxes are calculated the remaining parameters can be calculated.

In optimizing the design, the primary factors to consider are the thermal conductivity and thickness of material 16 and material 30, the temperature $T_4$, the temperature at the scale surface $T_{scale}$ and the power to the main heater. The goal is to maximize the temperature differential along the lengths of material 16 and material 30 as scale builds up on the surface exposed to the bulk fluid flow.

As an example it is assumed the available heater has an output of 200 W and the conductive block has a cross section measuring 10 mm×50 mm. Using the above equations it is possible to investigate the effects of changing $T_4$, $T_{scale}$, material 16, material 30, $\delta_1, \delta_2$ and then to ascertain the device configuration that best meets the design goal of maximizing the temperature differentials in the sensor.

Figure 12:
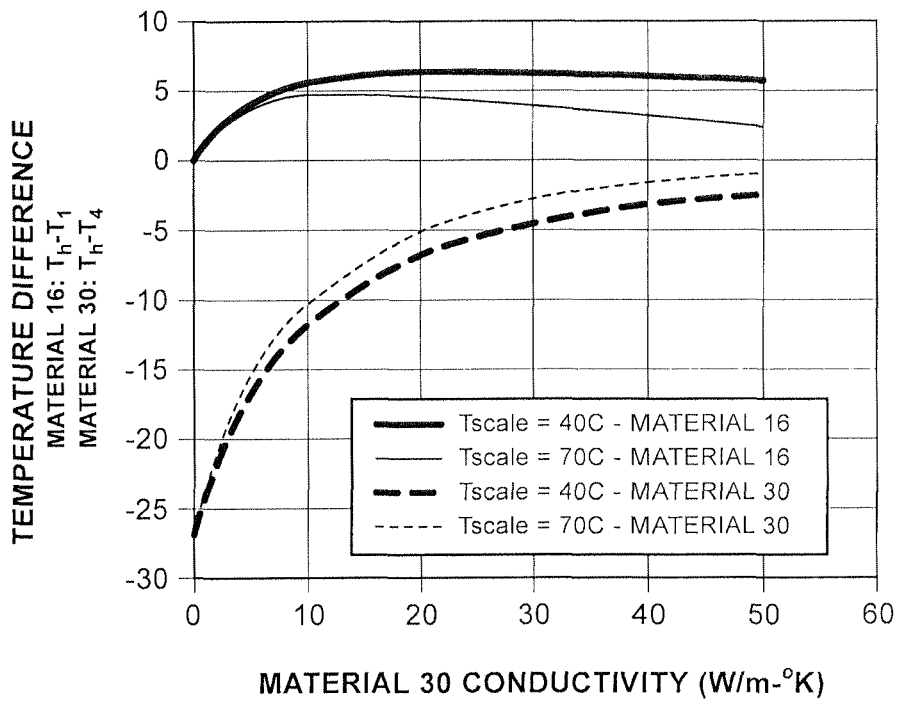
FIG. 12 is a graph showing the effect of material 30 conductivity on temperature difference with a scale formation of 200 microns.

FIG. 12 shows the effect of varying the thermal conductivity of material 30. The design could be optimized for maximizing the temperature differential in material 30, while ignoring the temperature differential in material 16. In this case, the thermal conductivity of material 30 would be as low as possible. The drawback is that the temperature difference in material 16 would not change significantly as scale developed. The figure shows that there is an optimum thermal conductivity for material 30, one that maximizes the temperature differential in material 16, i.e. $K_{30}$=~20 W/m-° K. For the purposes of this example the thermal conductivity of material 30 is set at 20 W/m-° K. The rationale is that it would be better to have two different temperature differences indicating scale growth rather than only one.

Figure 13:
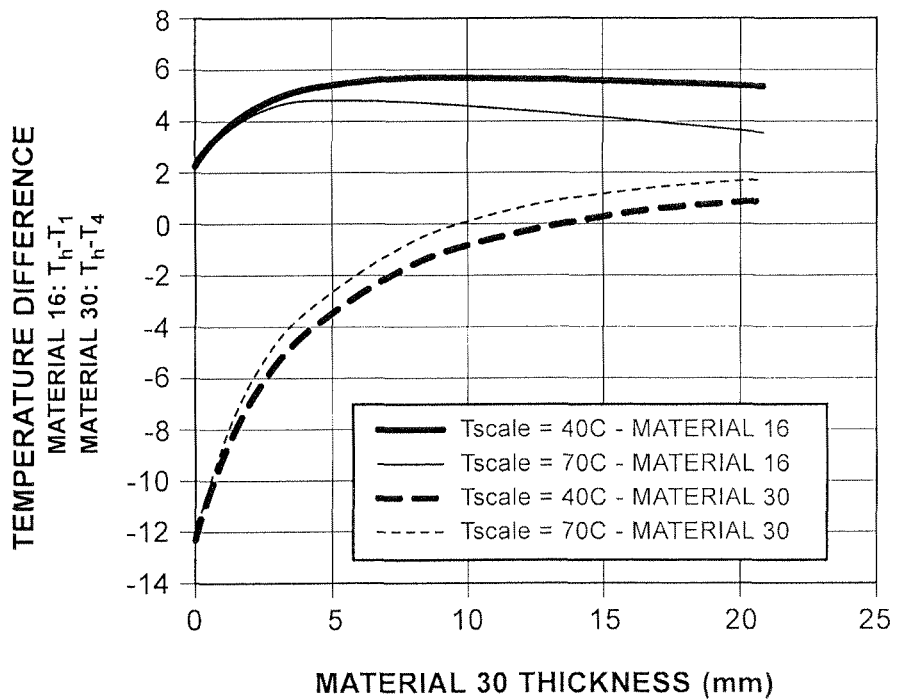
FIG. 13 is a graph showing the effect of material 30 thickness on temperature difference with 200 micron scale.

In FIG. 13 the effects of varying the thickness of Material 30 are examined. As the thickness of material 30 ($\delta_2$) is increased the effective thermal resistance increases, causing it to appear more like an insulator. Thus, the results are similar to those shown in FIG. 12. Again, there is an optimum thickness of material 30 ($\delta_2$) for maximizing the temperature difference in material 16. For maximizing the temperature difference in material 16, the thickness of material 30 is set at 10 mm.

Figure 14:
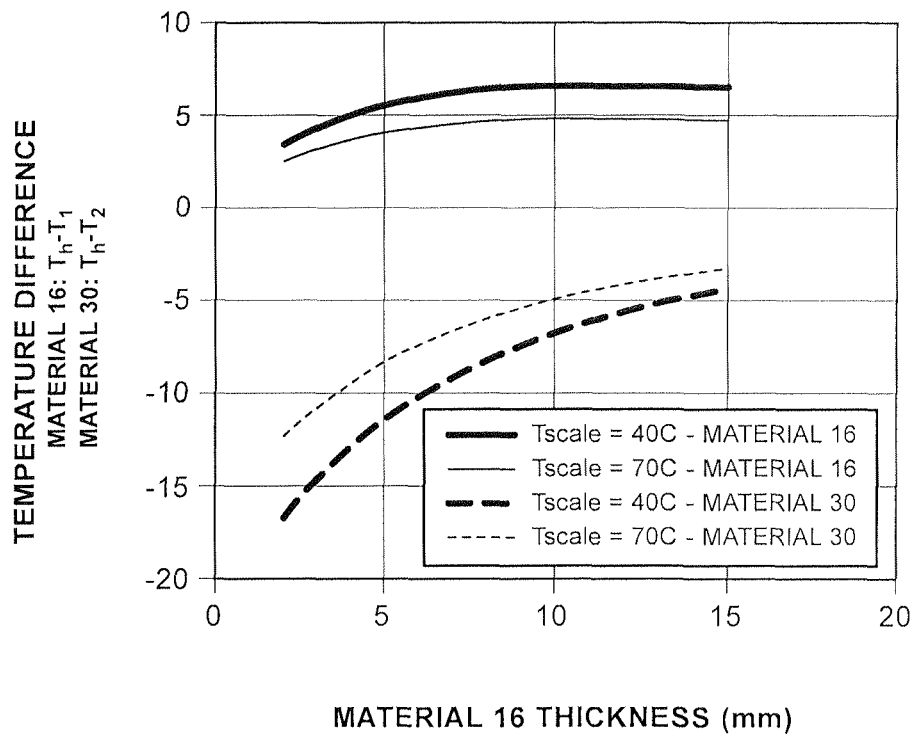
FIG. 14 is a graph showing the effect of material 16 thickness on temperature difference with 200 micron scale.

The thickness of material 16 is addressed in FIG. 14. The effect of increasing material 16 thickness plateaus at around $\delta_1$=~10 mm. At this thickness there is still a reasonable temperature difference across material 30, the thickness of material 16 is therefore set at 10 mm for the purposes of this example.

Figure 15:
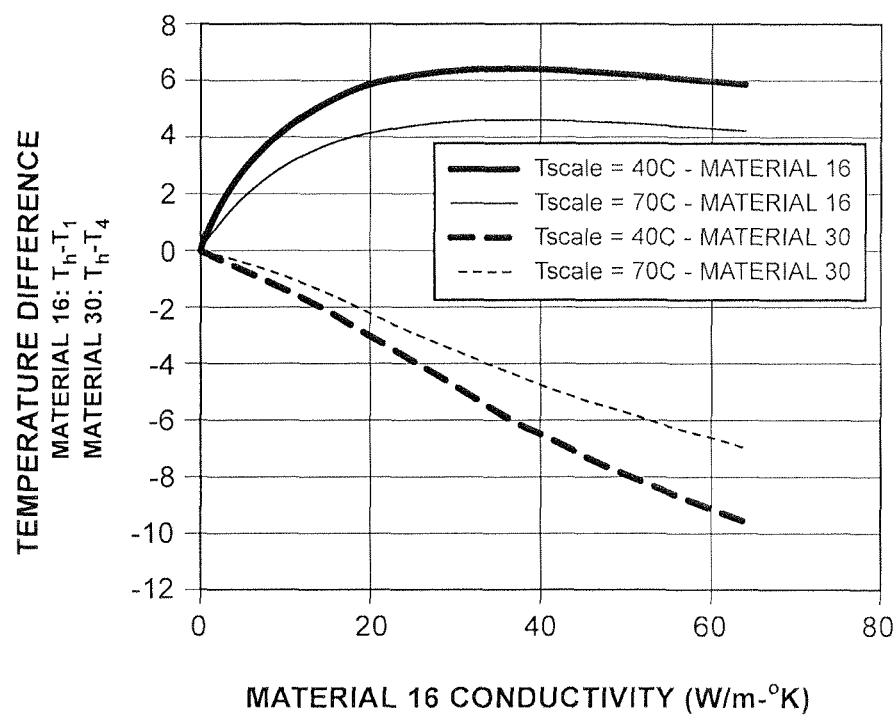
FIG. 15 is a graph showing the effect of material 16 conductivity on temperature difference with 200 micron scale.

In FIG. 15 the thermal conductivity of material 16 is considered. Since changing thickness has the effect of changing the thermal resistance, the results are similar to what occurred with material 30. The effect of increasing the thermal conductivity plateaus. The sensor used in the previously described scaling test had a thermal conductivity of ~42 W/m° K, which also provides a reasonable temperature difference across material 30, the thermal conductivity of material 16 is set to 42 W/m° K for the purposes of this example.

Figure 16:
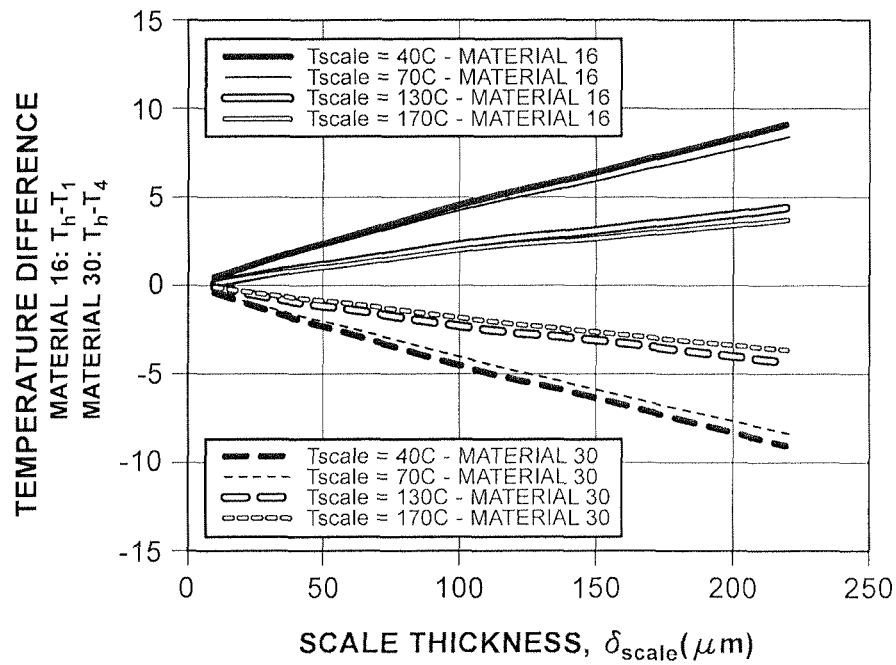
FIG. 16 is a graph showing the temperature differential vs. scale thickness.

FIG. 16 shows the temperature difference across both material 16 and material 30 for several different conditions and a range of scale thicknesses. The cases with $T_{scale}$ of 40 and 70 C are lower temperature applications, more common to what would be found in standard industrial heat exchanger applications. The temperature differences in both material 16 and material 30 are adequate for monitoring scale development. The results for the cases with $T_{scale}$ of 130 and 170 C are not as satisfactory. These cases are more representative of paper mill pulping and black liquor applications.

Figure 17:
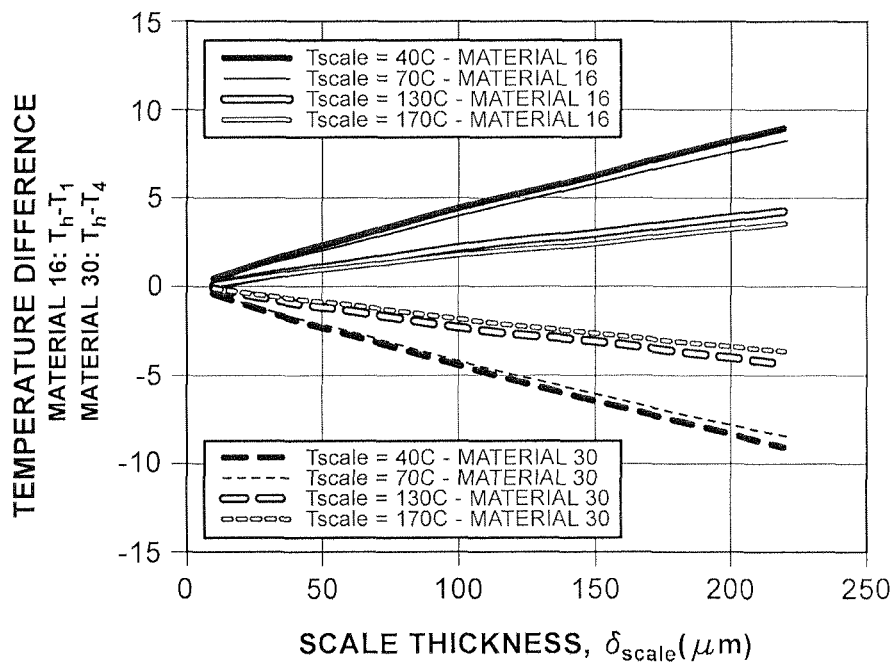
FIG. 17 is a graph showing the temperature differential vs. scale thickness wherein the temperature $T_4$ is varied.
Figure 18:
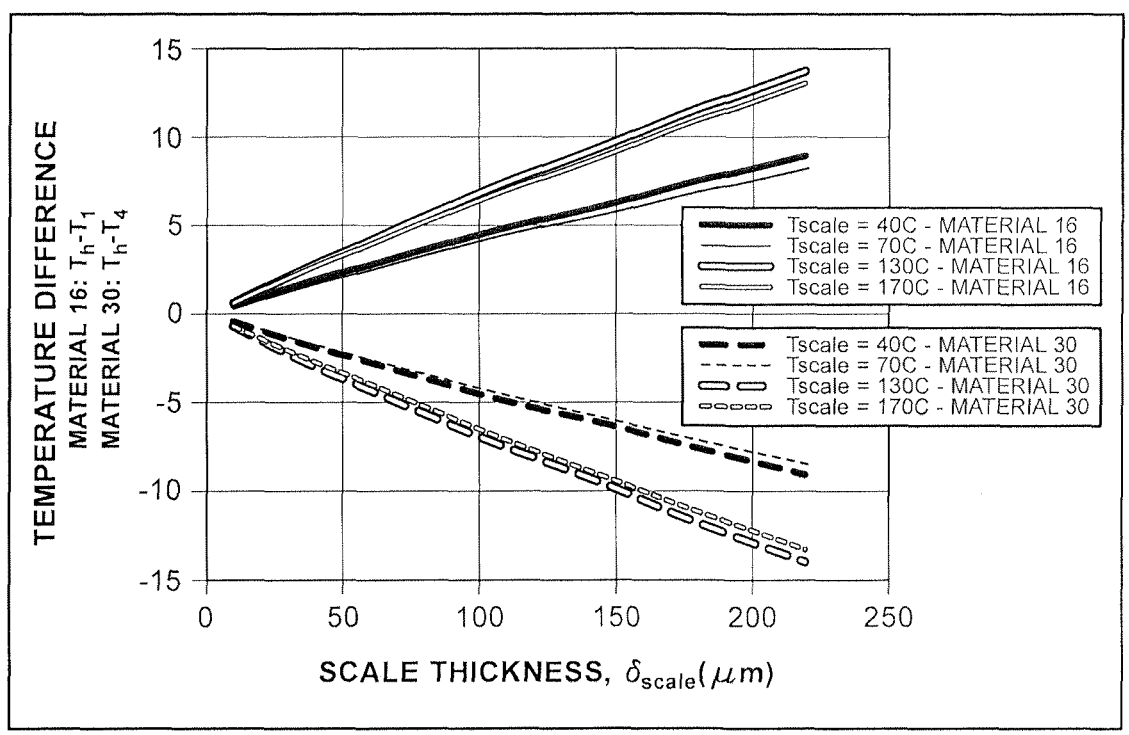
FIG. 18 is a graph showing the temperature differential with the same conditions as in FIG. 17 except in the high $T_{scale}$ cases the power to the heater is 500 watts instead of 200 watts.

FIG. 17 shows that utility of adjusting $T_4$ for a specific application. In all the previous graphs $T_4$ was set at 50 C. In FIG. 18, $T_4$ is set for the particular case

| | |
|---|---|
| $T_{scale}$=40 C→$T_4$=80 C | 1. |
| $T_{scale}$=70 C→$T_4$=100 C | 2. |
| $T_{scale}$=130 C→$T_4$=100 C | 3. |
| $T_{scale}$=170 C→$T_4$=130 C | 4. |

Adjusting $T_4$ up or down can expand or contract the range of the temperature differential as scale builds up. By adjusting $T_4$, control is being exerted over the heat transfer through the secondary heat flow path. The utility of the device depends on manipulating the temperatures inside the device to maximize the temperature differentials. In the high $T_{scale}$ cases the task can be made easier by providing more power to the heater, thus making it possible to increase $T_h$ for a given set of conditions. FIG. 18 shows the same conditions as FIG. 17, except in the high $T_{scale}$ cases the power to the heater is 500 W instead of 200 W.

Figure 4:
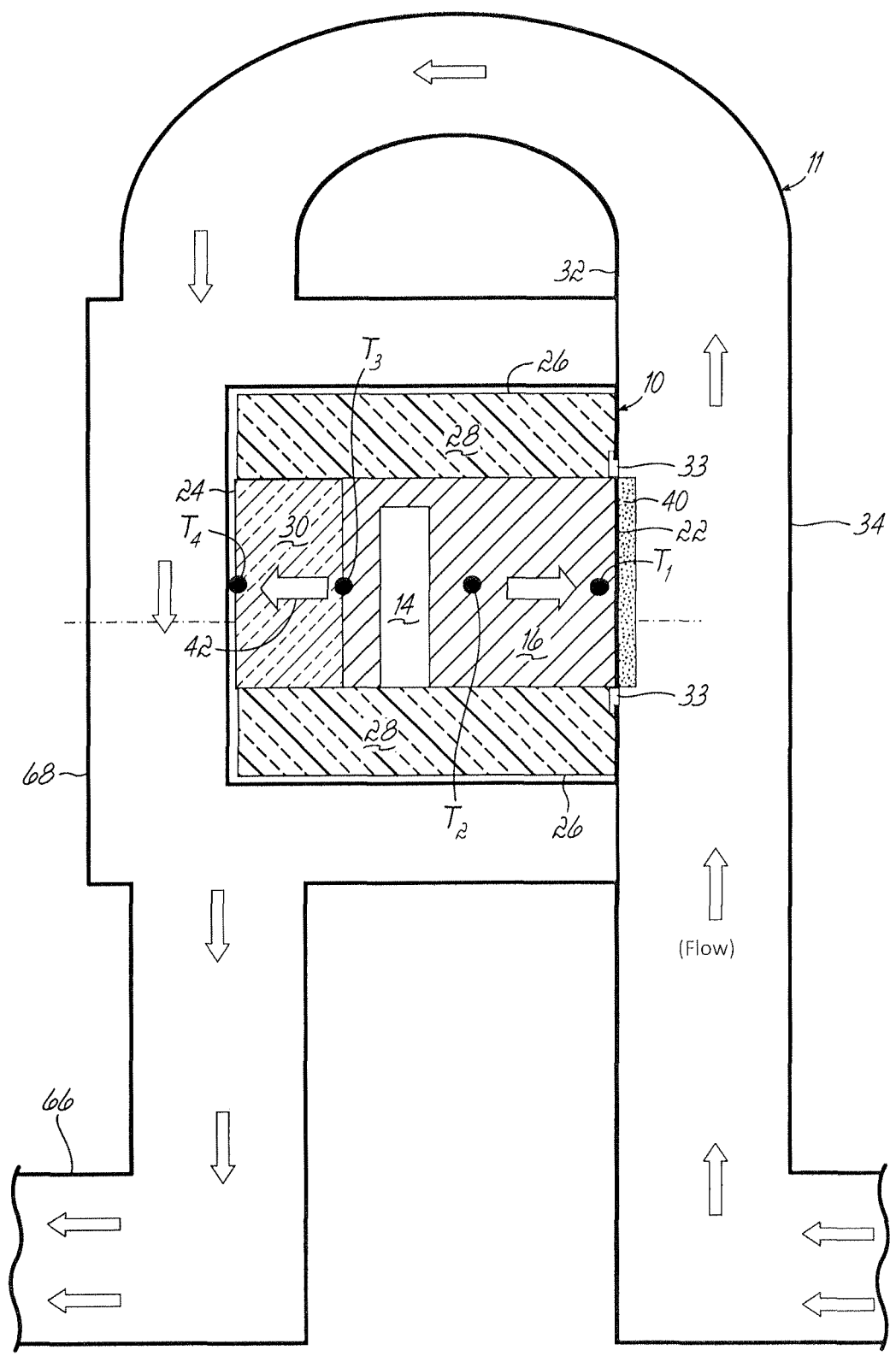
FIG. 4 is a cross sectional diagrammatic view of a third alternate embodiment of the present invention.

The embodiment shown in FIG. 4 is a modification of the embodiment shown in FIG. 1. The modification is intended to eliminate the impact of ambient condition changes and provide known conditions along the secondary heat conduction path by providing a nominally isothermal boundary condition. It also compensates for velocity and temperature changes in bulk fluid flow.

This is accomplished by enclosing the device and circulating the fluid from the water system around the entirety of the sensor device. The sensor 10 is surrounded by the fluid from the water system by running conduit 11 around the sensor 10, back to a return conduit 66. Conduit 11 enlarges at area 68 to allow working fluid to surround all sides of the sensor 10, except the portion of sensor 10 that comprises the heated wetted test surface 22 where scale accumulates, which is already in contact with the flow passing through conduit 11. The environment surrounding sensor 10 is thus at the same temperature as the fluid, and is maintained constant to the extent that the temperature of the fluid id maintained constant. While heat is lost to the bulk flow 36 as before through the heated wetted test surface 22, and from all exposed sides 26 and from the second end 24, the loss of heat through sides 26 and end 24 is now nearly constant, since the temperature of the bulk water flow 36 is generally nearly constant.

Because the bulk flow 36 is utilized for temperature control, but no external energy is added, this device can be considered to make use of semi active heat flux control.

The heat flux is governed by the equations $$\frac{q_{material1}}{A} = K\left(\frac{T_2 - T_1}{\delta_b}\right),$$

$$\frac{q_{material2}}{A} = K\left(\frac{T_3 - T_4}{\delta_d}\right),$$

$$\frac{q_{total}}{A} = \frac{q_{material1}}{A} + \frac{q_{material2}}{A}$$

Figure 5:
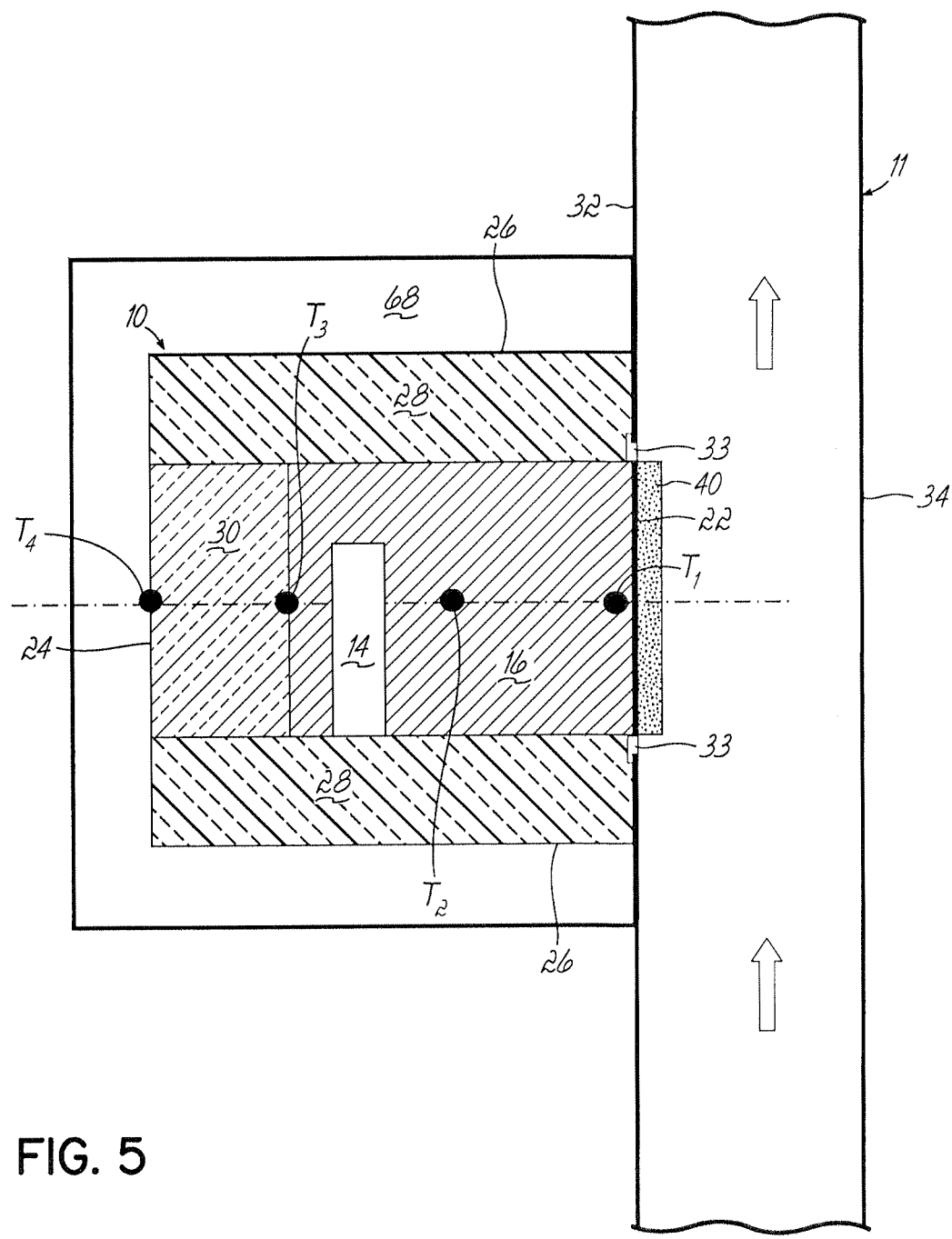
FIG. 5 is a diagrammatic cross sectional view of a fourth alternate embodiment of the present invention.

FIG. 5 shows a modified version of FIG. 1. It is intended to eliminate the impact of environmental changes by providing an isothermal boundary condition. In this case the device is surrounded by a second heater 68. Therefore, in a manner similar to the device shown in FIG. 4 there is heat flux control along the secondary heat conduction path. The heat flux control depicted schematically in FIG. 5 can be called active heat flux control, because it is supplied with a controlled amount of external energy. As such, the power supplied by secondary heater 68 may be adjusted or controlled by the temperature signal of $T_4$, which becomes a point of adjustment that can be used to optimize operation of the device when it must operate at more extreme conditions. A potential limitation of the device as depicted in FIG. 5 is the inability to cool surfaces 26 and 24 of sensor 10.

The heat flux is governed by the equations $$\frac{q_{material1}}{A} = K\left(\frac{T_2 - T_1}{\delta_b}\right),$$

$$\frac{q_{material2}}{A} = K\left(\frac{T_3 - T_4}{\delta_d}\right),$$

$$\frac{q_{total}}{A} = \frac{q_{material1}}{A} + \frac{q_{material2}}{A}$$

Figure 6:
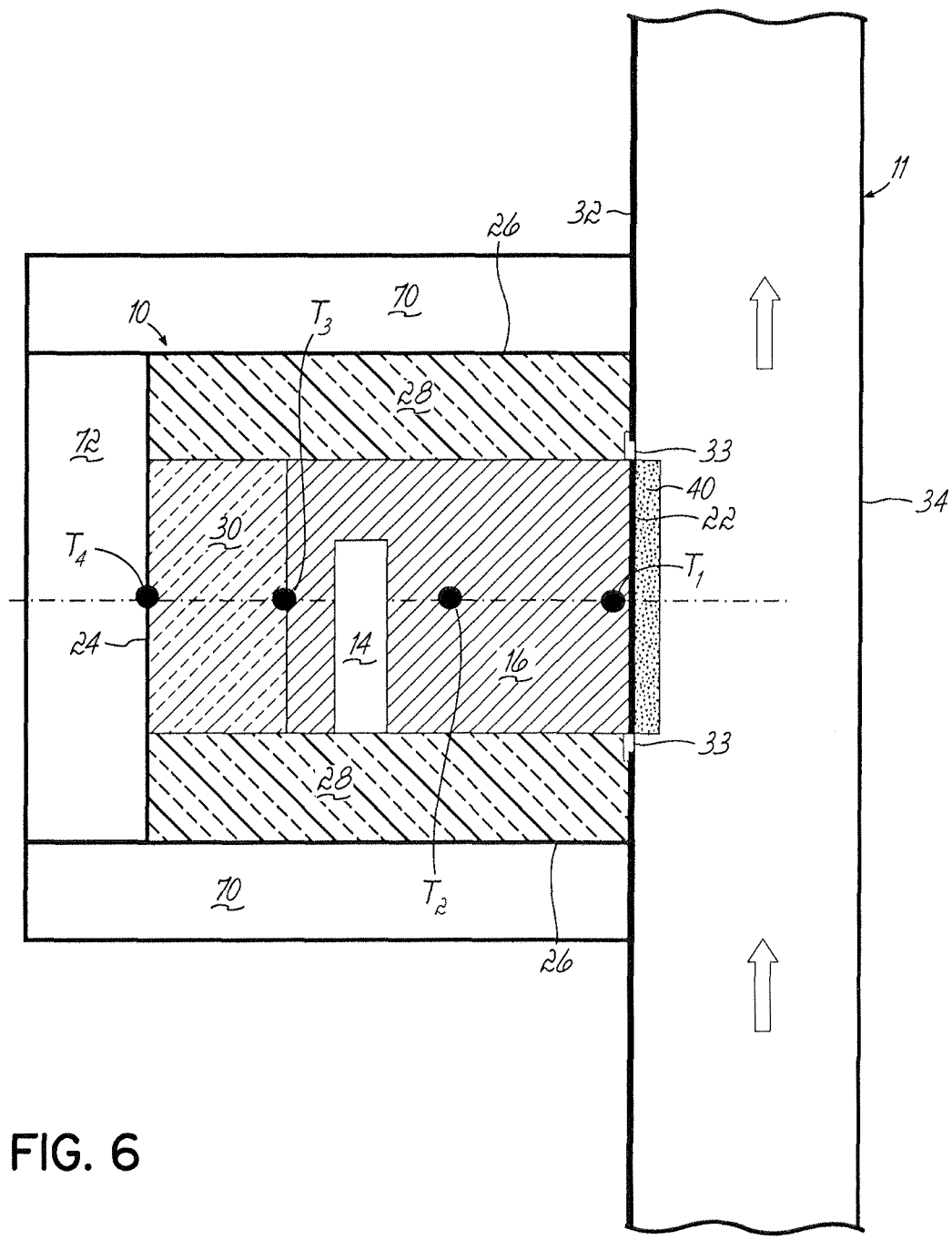
FIG. 6 is a diagrammatic cross sectional view of a fifth alternate embodiment of the present invention.

FIG. 6 shows a refinement of the embodiment shown in FIG. 5 in that there are now separate heaters 70 for the peripheral surfaces 26 of the sensor 10 and a separate heater 72 for second end 24. This embodiment has two distinct secondary heat conduction paths. This provides an enhanced capability for controlling heat flux both along the longitudinal axis and perpendicular to the longitudinal axis by controlling the temperatures along those surfaces. The heat flux control depicted schematically in FIG. 6 can be called active heat flux control along the secondary heat conduction paths, because it is supplied with a controlled amount of external energy. As such, the power supplied by the secondary heaters 70 and 72 are independently and collectively adjustable to maintain a constant temperature at $T_4$ or other potential temperature measurement locations, and can be used for further optimize operation of the device when it must operate at more extreme conditions. A potential limitation of the device as depicted in FIG. 6 is the inability to cool surfaces 26 and 24.

The heat flux is governed by the equations $$\frac{q_{material1}}{A} = K\left(\frac{T_2 - T_1}{\delta_b}\right),$$

$$\frac{q_{material2}}{A} = K\left(\frac{T_3 - T_4}{\delta_d}\right),$$

$$\frac{q_{total}}{A} = \frac{q_{material1}}{A} + \frac{q_{material2}}{A}$$

Figure 7:
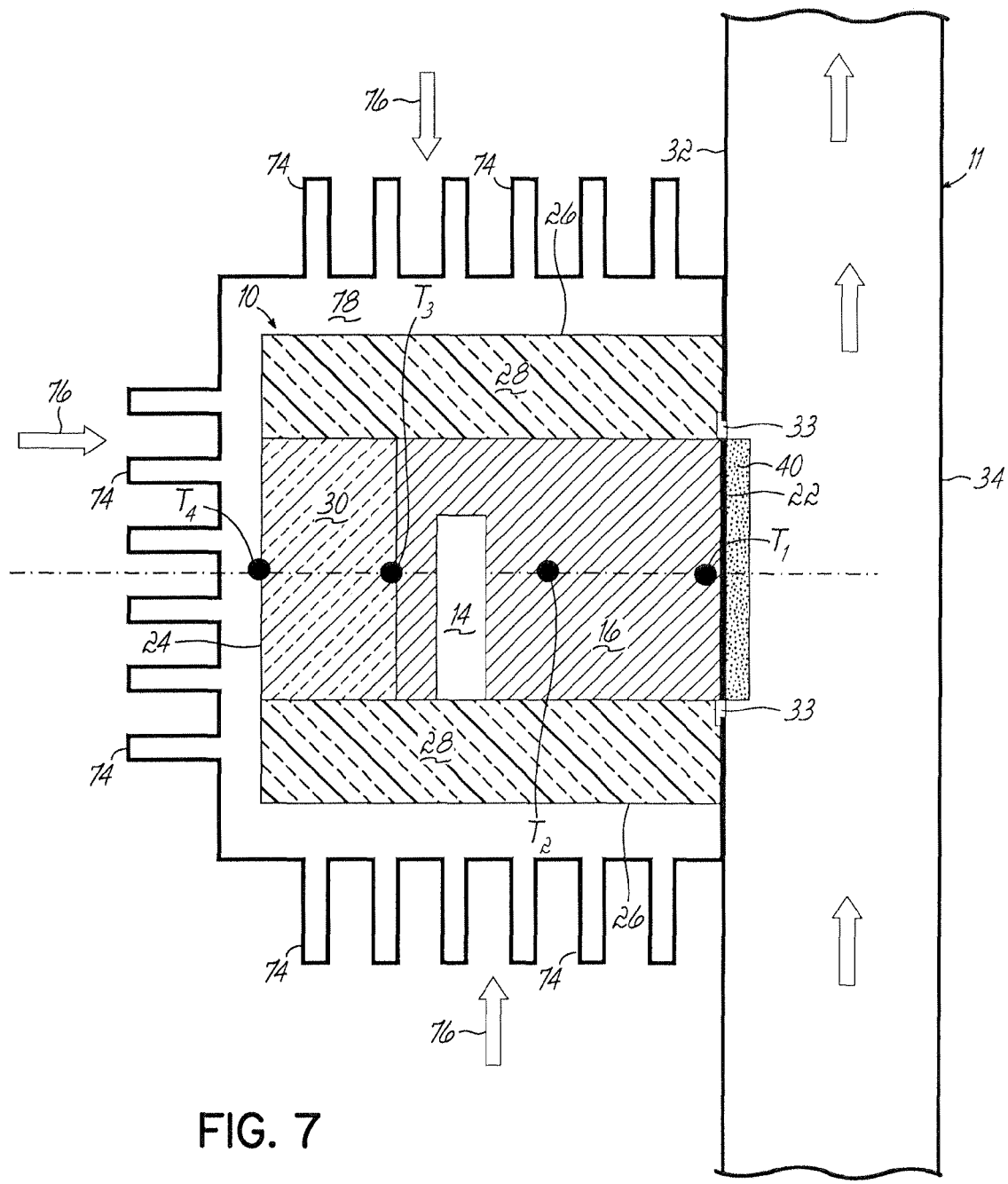
FIG. 7 is a diagrammatic cross sectional view of a sixth alternate embodiment of the present invention.

The embodiment shown by FIG. 7 uses active control of heat flux along the secondary heat conduction paths. In this case the device is surrounded by a variable heat sink 78, here represented by cooling fins 74 and a means of forcing air over the variable heat sink (not shown) which forces air in the direction of arrow 76. Heat removal is altered by increasing or decreasing the rate of air flow over the fins. It is also conceivable that a hot air flow could be used to reduce heat flux from the device. A more refined version would have separate heat flux control for the longitudinal surfaces of the device. A yet more refined version would have a water mist of adjustable magnitude sprayed on the variable heat sink surface to control the temperature of the exterior surfaces of sensor 10 even more effectively under even more extreme environmental conditions. The heat flux control depicted schematically in FIG. 7 can be called active heat flux control along the secondary heat conduction paths, because it is supplied with a controlled amount of external energy. As such, the set point of the air flow temperature or volume or run duration and/or water mist flow and/or duration are independently and collectively adjustable to further optimize operation of the device when it must operate at more extreme conditions, by providing means to further reduce the effect of changing ambient conditions.

The heat flux is governed by the equations $$\frac{q_{material1}}{A} = K\left(\frac{T_2 - T_1}{\delta_b}\right),$$

$$\frac{q_{material2}}{A} = K\left(\frac{T_3 - T_4}{\delta_d}\right),$$

$$\frac{q_{total}}{A} = \frac{q_{material1}}{A} + \frac{q_{material2}}{A}$$

Figure 8:
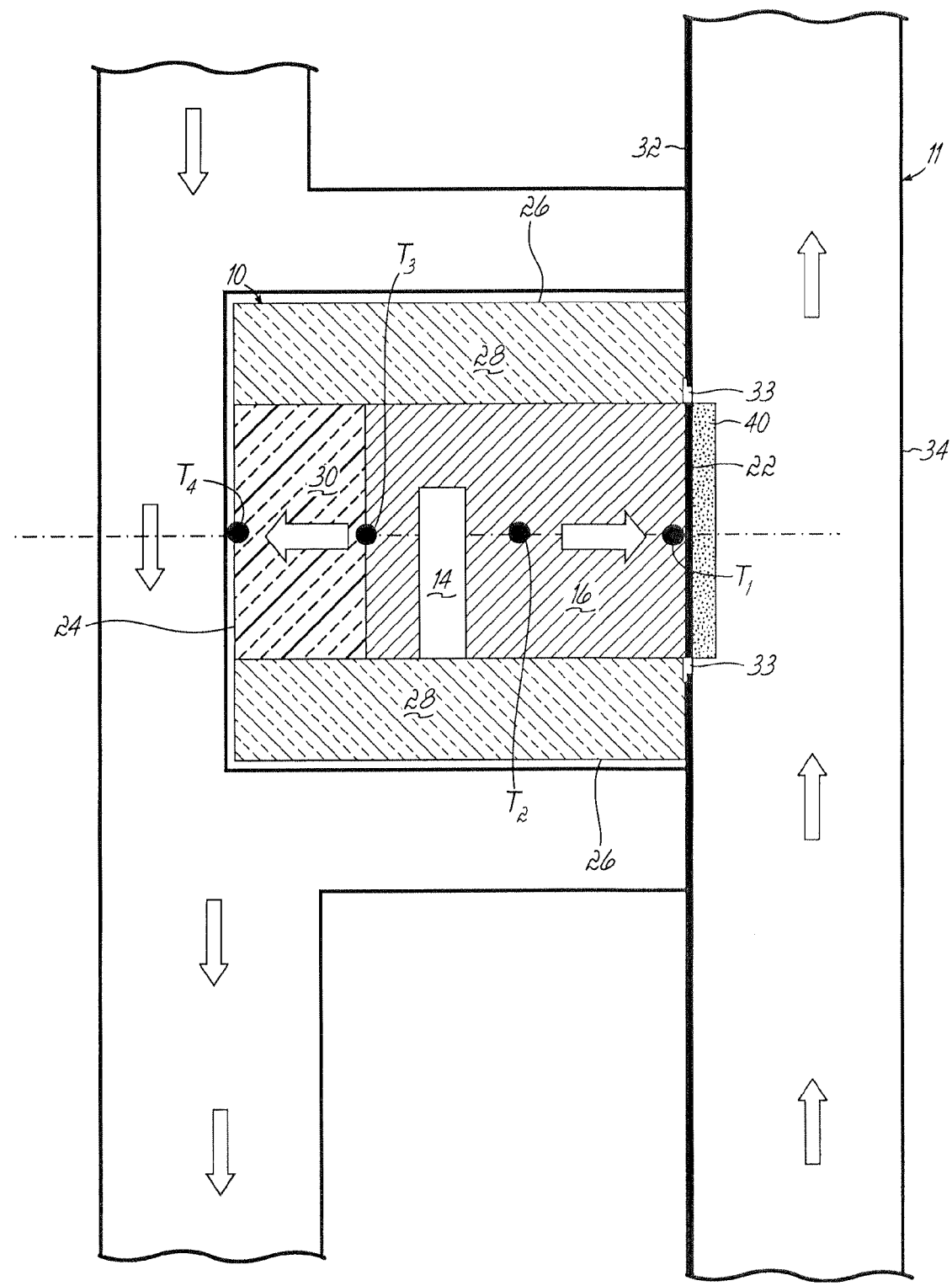
FIG. 8 is a diagrammatic cross sectional view of a seventh alternate embodiment of the present invention.

The embodiment shown in FIG. 8 is similar to the embodiment shown in FIG. 4. It uses a separate fluid flow to actively heat or cool the device. Therefore, this implementation provides the capability to control heat flux through temperature control, i.e., using a fluid at a specific temperature and to control heat flux directly, i.e., by changing the rate of fluid flow and thus the heat removed from or added to the device. The heat flux control depicted schematically in FIG. 8 can be called active heat flux control along the secondary heat conduction path, because it is supplied with a controlled amount of external energy. As such, the temperature set point and/or the flow rate of the separate working fluid are independently and collectively adjustable to further optimize operation of the device when it must operate at more extreme conditions, by providing means to further reduce the effect of changing ambient conditions.

The heat flux is governed by the equations $$\frac{q_{material1}}{A} = K\left(\frac{T_2 - T_1}{\delta_b}\right),$$

$$\frac{q_{material2}}{A} = K\left(\frac{T_3 - T_4}{\delta_d}\right),$$

$$\frac{q_{total}}{A} = \frac{q_{material1}}{A} + \frac{q_{material2}}{A}$$

Figure 11:
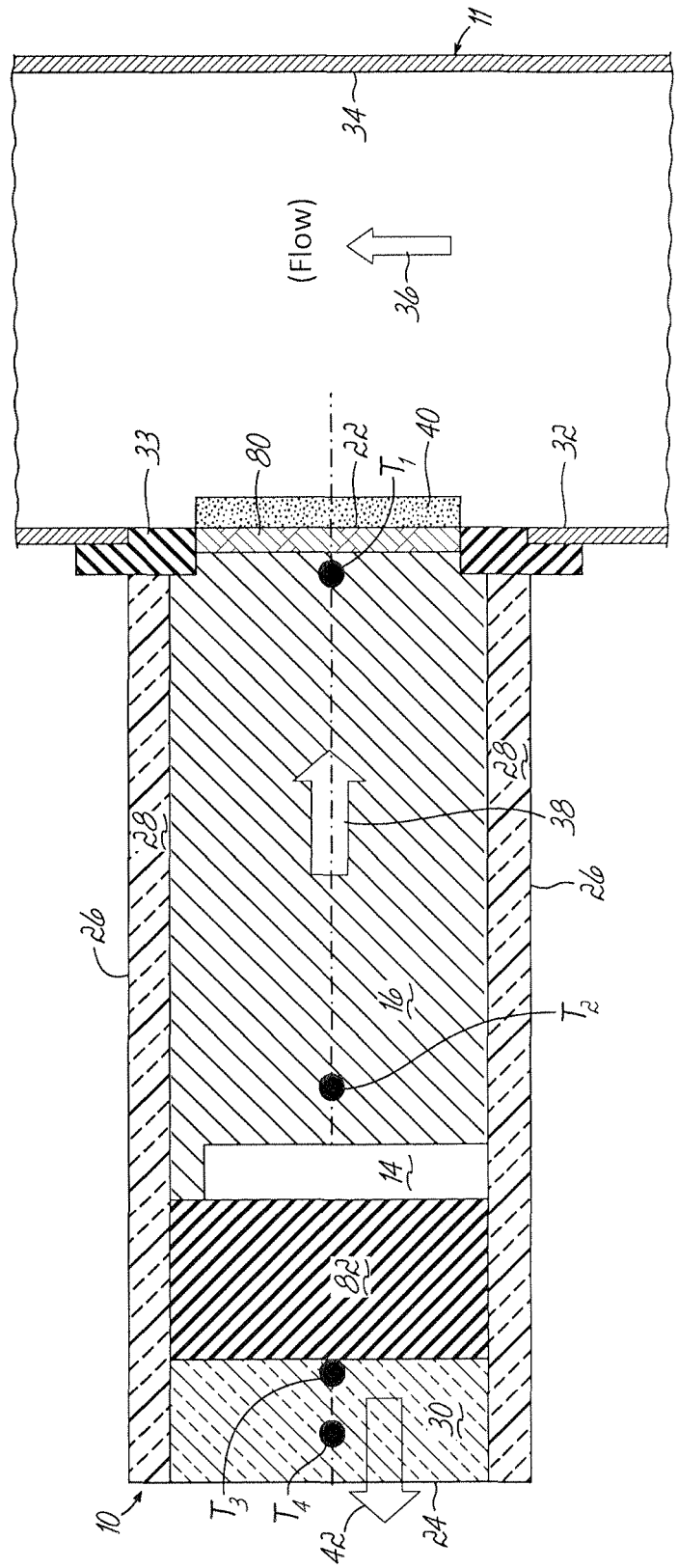
FIG. 11 is a diagrammatic cross section of an alternative embodiment of the heated conductive block component of the present invention.

FIG. 11 shows a diagrammatic cross section of an alternative embodiment of a component of the invention, conductive block 16. In FIG. 11, the conductive block 16 is comprised of a highly conductive material surrounding or partially surrounding the heating means 14, a second material 80 attached to the first material as the heated wetted test surface 22, and a third material 82 attached to the opposite end 24. The first material is chosen for its high heat conductivity, and could be copper, gold, silver, CuNi alloy, brass, aluminum, or any other highly conductive material. The use of a highly conductive material in this position facilitates good heat transfer in the direction indicated by arrow 38, to minimize the power required for heater 14 to produce the target temperature at the heated wetted test surface 22. Such a highly conductive material may not be appropriately corrosion resistant for exposure to the fluid in conduit 11 in some applications. The second material layer 80 is thin and is chosen for corrosion resistance, biofilm resistance, or to match the heat transfer surface of the heat transfer surface to be emulated. Since it is thin, its heat transfer characteristics are less critical. The third material 82 is chosen for its lower heat conductivity and adequate structural properties, and could be mild steel, stainless steel, or any plastic with sufficient structural strength to serve its mechanical needs at the anticipated temperature. It is chosen to resist the flow of heat in the direction of the secondary heat conduction path.

The materials may be bonded together by any appropriate mechanical means such as screws or bolts, clamps, or the like, by welding, brazing, or other appropriate techniques for the particular metals. Of particular interest is a foil brazing technique, which can bond a variety of metal types well.

In each of the embodiments shown in FIGS. 3 through 8 and 11, an apparatus, as shown in FIG. 2 used to measure the thickness of the deposited scale, can be incorporated in the same manner as in FIG. 2. In each of these embodiments, the scale measuring sensor 10 would determine the fouling factor of deposited scale. In each of these, as inverse soluble scale accumulates on the heated wetted test surface 22, the scale 40 provides an additional restriction to heat flow path through the metal block 16 through the heated wetted test surface 22 to the bulk flow. The rising the temperature in the block is registered by both temperature sensors. With a higher internal temperature, more heat exits via the provided partially insulated heat flow path to the atmosphere. This results in a reduced temperature differential between the two temperature sensors because less heat is exiting through the heated wetted test surface 22. The fouling factor, or reduction in heat flow through the heated wetted metal surface indicates the accumulated scale. The temperature differential between the two temperature sensors is linear with respect to scale thickness for any particular type of scale. The temperature differential between the two temperature sensors is different for different types of scale. By measuring the scale thickness, such as by pulsed ultrasonic signal, one can ascertain the type of scale deposited and, in turn, provide the most effective treatment.

This has been a description of the present invention along with the preferred method of practicing the present invention. However, the invention itself should only be defined by the appended claims, Wherein we claim:

1. A method of detecting fouling or scaling of a heated wetted test surface comprising heating a conductive block using a heater;
said conductive block having a first end comprising said heated wetted test surface, and a second end opposite said first end;
contacting said heated wetted test surface with a first liquid;
measuring the temperatures at first and second positions along said conductive block wherein said first position is closer to said heated wetted test surface than said second position to obtain first and second temperature measurements;
comparing first and second temperature measurements at said first and second positions to establish a reference temperature difference with no fouling or scaling on said heated wetted test surface;
determining fouling or scaling on said surface by subsequently measuring temperatures at said first and second positions and detecting changes in temperature differences between said temperatures at said first and second positions relative to said reference temperature difference.

2. The method claimed in claim 1 wherein said first and second positions are between said heater and said heated wetted test surface.

3. The method claimed in claim 1, wherein said first and second positions are between said heater and said second end opposite said first end.

4. The method claimed in claim 1, further comprising providing a first material around a peripheral surface of said conductor and providing a second material at said second end wherein said first and second materials have different heat conduction coefficients.

5. The method claimed in claim 1, wherein a flow rate of scale control chemicals is adjusted in response to changes in heat conductivity of accumulating scale on said heated wetted test surface.

6. The method claimed in claim 1, further comprising measuring the thickness of deposits on said wetted surface.

7. The method claimed in claim 6, wherein said thickness is measured using sound waves.

8. The method claimed in claim 1, further comprising providing insulation around a peripheral surface of said conductive block whereby heat resistance is greater radially outward from said conductor than from said conductive block than through said second end.

9. The method claimed in claim 8, further comprising adjusting a temperature of said exterior surfaces utilizing a heat exchange fluid surrounding said exterior surfaces.

10. The method claimed in claim 9, further comprising controlling the temperature of said exterior surfaces by adjusting the flow or temperature of said heat exchange fluid.

11. The method claimed in claim 10, wherein said heat exchange fluid is the same as said first liquid.

12. The method claimed in claim 1, further comprising at least partially surrounding said first and second materials with a heat sink.

13. The method claimed in claim 12, further comprising projecting a heat exchange fluid over said heat sink to control the temperature of said exterior surfaces.

14. The method claimed in claim 13, further comprising controlling said heat exchange fluid to establish a desired temperature of said exterior surface.

15. The method claimed in claim 13, wherein said heat exchange fluid comprises at least one of air and a water mist.

16. An apparatus to detect fouling or scale on a heated wetted test surface wherein said heated wetted test surface is in a liquid flow path in contact with a bulk liquid comprising;
a heater;
a conductive block having a first end comprising said heated wetted test surface and a second end opposite said first end and a peripheral surface;
a first temperature sensor within said conductive block at a first position close to said heated wetted test surface;

a second temperature sensor within said conductive block at a second position close to said heater and further from said heated wetted test surface than said first temperature sensor; wherein said second end has a higher heat conductivity than said peripheral surface.

17. The apparatus claimed in claim 16, wherein said first and second positions are offset sufficiently to avoid interference with heat flux.

18. The apparatus claimed in claim 16, wherein said apparatus further includes a device operable to measure scale thickness on said heated wetted test surface by directing wave energy against said wetted surface.

19. The apparatus claimed in claim 16, wherein said apparatus is at least partially surrounded by heat exchange fluid.

20. The apparatus claimed in claim 16, further comprising a second heater at said second end.

21. The apparatus claimed in claim 16, further comprising a third heater in contact with at least a portion of said peripheral surface.

22. The apparatus claimed in claim 16, wherein at least one of said peripheral surface and said second end includes insulation.

23. The apparatus claimed in claim 22, wherein said peripheral surface is at least partially surrounded by a heat sink.

24. The apparatus claimed in claim 16, wherein said conductive block comprises a first material and has a thin layer of a second material bonded to said first end wherein said layer of second material comprises said heated wetted test surface.

25. The apparatus claimed in claim 24, wherein said second material comprises a corrosion resistant material.

26. The apparatus claimed in claim 16, wherein said conductive block is a layer of a third material at said second end wherein said third material has a different thermal conductivity than a thermal conductivity of said first mate.

27. An apparatus to detect fouling or scale on a heated welted test surface wherein said heated wetted test surface is in a fluid flow path comprising;
   a heater;
   a conductive block having a first end comprising said heated wetted test surface and a second end opposite said first end and a peripheral surface;
   a first temperature sensor within said conductive block close to said heater and between said heater and said second end;
   a second temperature sensor within said conductive block at a second position between said heater and said second end and close to said second end but further from said heater than said first temperature sensor.

* * * * *